(12) United States Patent
Kanno

(10) Patent No.: US 8,975,434 B2
(45) Date of Patent: Mar. 10, 2015

(54) METHOD FOR PRODUCING CYCLOPENTANONE COMPOUND, AND INTERMEDIATE COMPOUND

(75) Inventor: Hisashi Kanno, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 14/123,323

(22) PCT Filed: Jun. 4, 2012

(86) PCT No.: PCT/JP2012/064406
§ 371 (c)(1),
(2), (4) Date: Dec. 2, 2013

(87) PCT Pub. No.: WO2012/169468
PCT Pub. Date: Dec. 13, 2012

(65) Prior Publication Data
US 2014/0107372 A1    Apr. 17, 2014

(30) Foreign Application Priority Data

Jun. 7, 2011 (JP) ................................. 2011-127764

(51) Int. Cl.
| | | |
|---|---|---|
| C07C 69/75 | (2006.01) | |
| C07C 49/457 | (2006.01) | |
| C07C 45/61 | (2006.01) | |
| C07C 309/66 | (2006.01) | |
| C07C 309/73 | (2006.01) | |
| C07C 69/757 | (2006.01) | |
| C07C 49/567 | (2006.01) | |
| C07C 67/31 | (2006.01) | |
| C07C 67/307 | (2006.01) | |
| C07C 67/343 | (2006.01) | |
| C07C 45/65 | (2006.01) | |
| C07C 45/67 | (2006.01) | |

(52) U.S. Cl.
CPC ............... *C07C 45/61* (2013.01); *C07C 309/66* (2013.01); *C07C 309/73* (2013.01); *C07C 69/757* (2013.01); *C07C 49/567* (2013.01); *C07C 67/31* (2013.01); *C07C 67/307* (2013.01); *C07C 67/343* (2013.01); *C07C 45/65* (2013.01); *C07C 45/676* (2013.01); *C07C 2101/08* (2013.01)
USPC ............................................. 560/53; 568/330

(58) Field of Classification Search
CPC .... C07C 67/307; C07C 67/343; C07C 45/61; C07C 45/676
See application file for complete search history.

(56) References Cited

U.S. PATENT DOCUMENTS

| | | | |
|---|---|---|---|
| 4,938,792 A | 7/1990 | Kumazawa et al. | |
| 5,028,254 A | 7/1991 | Kumazawa et al. | |
| 5,159,118 A | 10/1992 | Kumazawa et al. | |
| 5,239,089 A | 8/1993 | Kumazawa et al. | |
| 5,414,105 A | 5/1995 | Kumazawa et al. | |
| 5,519,160 A | 5/1996 | Obara et al. | |
| 5,681,979 A | 10/1997 | Hoshi et al. | |
| 7,166,750 B1 | 1/2007 | Sunagawa et al. | |
| 2002/0013489 A1 | 1/2002 | Wong | |
| 2012/0232286 A1 | 9/2012 | Araki et al. | |
| 2014/0200352 A1 | 7/2014 | Araki et al. | |
| 2014/0213794 A1 | 7/2014 | Araki et al. | |

FOREIGN PATENT DOCUMENTS

| | | |
|---|---|---|
| CN | 102639509 A | 8/2012 |
| EP | 0 731 083 A1 | 9/1996 |

(Continued)

OTHER PUBLICATIONS

International Search Report issued in PCT/JP2012/064406 mailed Jul. 10, 2012.

(Continued)

*Primary Examiner* — Paul A Zucker
(74) *Attorney, Agent, or Firm* — Birch, Stewart, Kolasch & Birch, LLP

(57) ABSTRACT

In order to provide a novel method for producing a cyclopentanone compound, the present invention is a method for producing a cyclopentanone compound represented by the formula (I). The method includes the steps of: substituting the group represented by Y by a hydrogen atom by allowing a compound represented by the formula (III) or an intermediate compound obtained from the compound represented by the formula (III) to react with a catalyst or a halogenating agent; and substituting, by hydrogen atoms, (i) the group or the atom represented by $Z^1$ and (ii) the group or the atom represented by $Z^2$, by reducing the compound represented by the formula (III) or the intermediate compound obtained from the compound represented by the formula (III).

[Chem. 1]

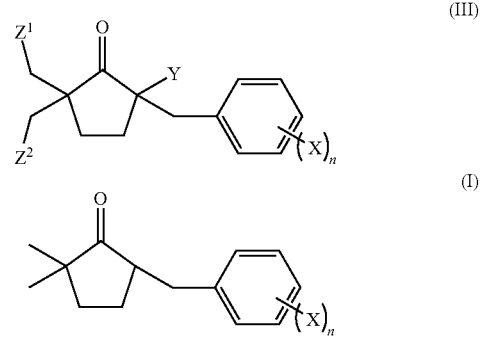

12 Claims, 1 Drawing Sheet

(56) References Cited

FOREIGN PATENT DOCUMENTS

| | | |
|---|---|---|
| JP | 1-93574 A | 4/1989 |
| JP | 5-65243 A | 3/1993 |
| JP | 5-271197 A | 10/1993 |
| JP | 7-82219 A | 3/1995 |
| JP | 8-245517 A | 9/1996 |
| JP | 9-278707 A | 10/1997 |
| JP | 2004-501894 A | 1/2004 |
| WO | WO 01/12580 A1 | 2/2001 |
| WO | WO 2011/070771 A1 | 6/2011 |

OTHER PUBLICATIONS

First Office Action issued Sep. 22, 2014, in Chinese Patent Application No. 201280028053.3, with English translation.
English translation of International Preliminary Report on Patentability and Written Opinion issued Dec. 27, 2013, in PCT International Application No. PCT/JP2012/064406.
Extended European Search Report issued Oct. 20, 2014, in European Patent Application No. 12796426.0.

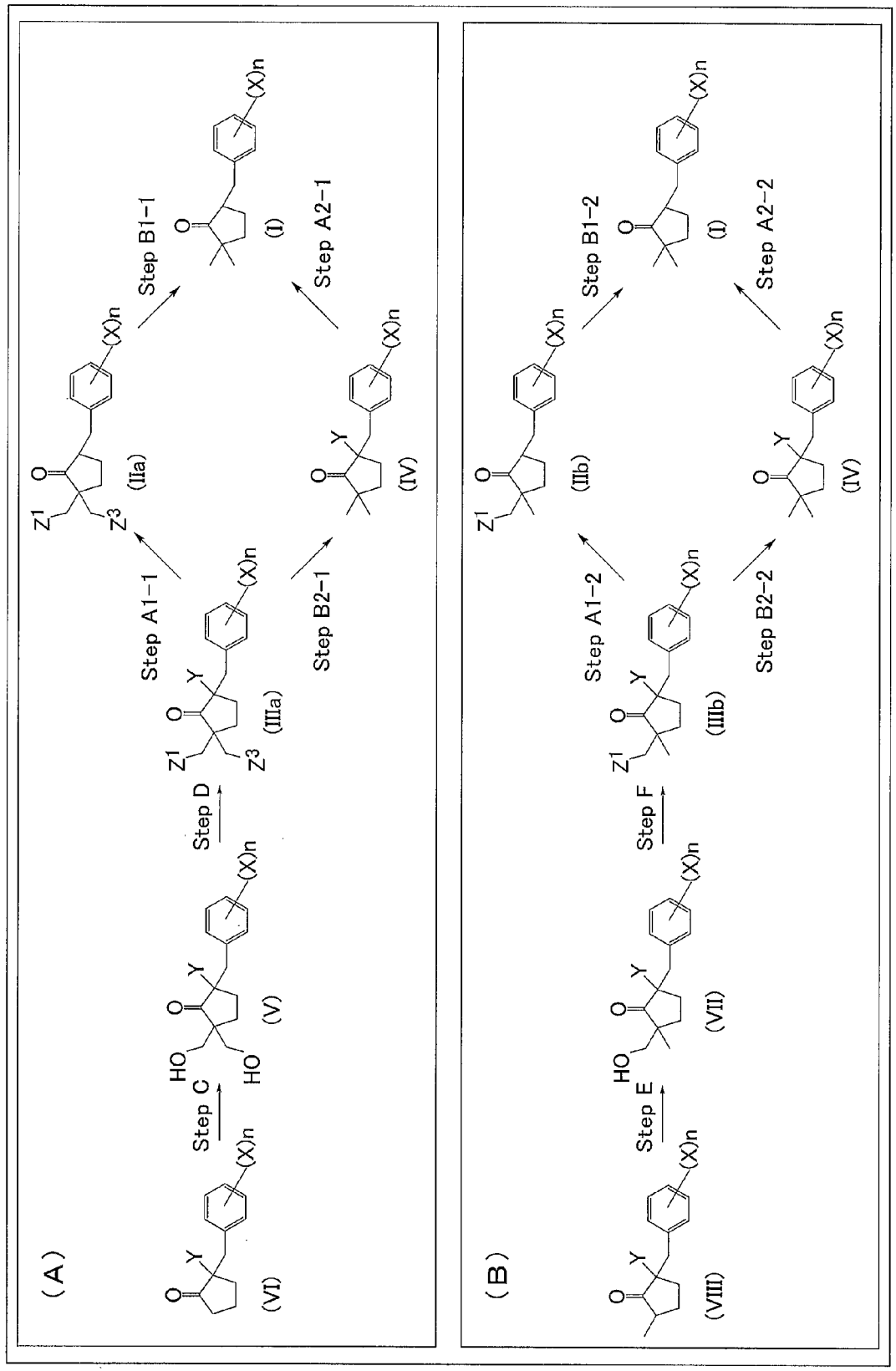

METHOD FOR PRODUCING CYCLOPENTANONE COMPOUND, AND INTERMEDIATE COMPOUND

TECHNICAL FIELD

The present invention relates to a method for producing a cyclopentanone compound and an intermediate compound for the cyclopentanone compound. Specifically, the present invention relates to (i) a method for producing 5-((substituted or unsubstituted)benzyl)-2,2-dimethylcyclopentanone and (ii) an intermediate compound for 5-((substituted or unsubstituted)benzyl)-2,2-dimethylcyclopentanone.

BACKGROUND ART

Metconazole is an agricultural fungicide which is sold and used in many countries around the world. As a method for producing 5-((substituted or unsubstituted)benzyl)-2,2-dimethylcyclopentanone which is an intermediate for production of metconazole and its analogs, there have been known methods described in Patent Literatures 1 to 7.

CITATION LIST

Patent Literature

Patent Literature 1
Japanese Patent Application Publication, Tokukaihei, No. 01-093574 A (1989)
Patent Literature 2
Japanese Patent Application Publication, Tokukaihei, No. 05-065243 A (1993)
Patent Literature 3
International Publication WO01/012580
Patent Literature 4
Japanese Patent Application Publication, Tokukaihei, No. 07-082219 A (1995)
Patent Literature 5
Japanese Translation of PCT International Application Tokuhyo No. 2004-501894 A
Patent Literature 6
Japanese Patent Application Publication, Tokukaihei, No. 08-245517 A (1996)
Patent Literature 7
Japanese Patent Application Publication, Tokukaihei, No. 09-278707 A (1997)

SUMMARY OF INVENTION

Technical Problem

A production method described in Patent Literature 1 or 2 includes a reaction in which 1-((substituted or unsubstituted)benzyl)-2-oxocyclopentanecarboxylic acid methyl ester is alkylated with an alkyl halide and sodium hydride. A production method described in Patent Literature includes a reaction in which 3-methyl-1-((substituted or unsubstituted)benzyl)-2-oxocyclopentanecarboxylic acid methyl ester is alkylated with an alkyl halide and sodium hydride. A production method described in Patent Literature includes a reaction in which 2-oxocyclopentanecarboxylic acid methyl ester is alkylated with an alkyl halide and sodium hydride. A production method described in Patent Literature includes a reaction for causing, with use of 4-chlorobenzyl chloride and sodium hydride, 5-cyano-2,2-dimethylcyclopentanone to be subjected to benzylation. As is clear from above, all the production methods described in Patent Literatures 1 to 5 use sodium hydride.

Since sodium hydride undergoes exothermic reaction to generate hydrogen, there is a risk that an accident may occur unless the reaction is controlled carefully. Furthermore, also when the reagent is stored or handled, the reagent may react with water in the air and, in some cases, may ignite. In order to ensure safety in production and avoid a risk of handling, there has been a demand for development of a safer method for producing 5-((substituted or unsubstituted)benzyl)-2,2-dimethylcyclopentanone without the use of sodium hydride.

Patent Literature 6 describes a method for producing 1-(4-chlorobenzyl)-3,3-dimethyl-2-oxocarboxylic acid methyl ester by allowing 1-(4-chlorobenzyl)-3-methyl-2-oxocarboxylic acid methyl ester to react with, in the presence of molecular sieves, methyl bromide and sodium hydroxide pulverized in a mortar.

The method described in Patent Literature 6 is not necessarily suitable for industrial use because, for example, sodium hydroxide needs to be pulverized before use and the molecular sieve, which is solid, needs to be removed after the reaction. Furthermore, methyl bromide is an ozone-depleting substance, and therefore the usage of methyl bromide is restricted by the Montreal Protocol. Therefore, it has been desirable to use methyl bromide as little as possible.

Patent Literature 7 describes a production method which does not use sodium hydride, methyl bromide or the like. However, it cannot be said that the method is excellent from industrial point of view because, for example, the method uses expensive $BF_3$. Therefore, there has been a demand for development of a better production method.

The present invention has been made in view of the above problems, and an object of the present invention is to provide a novel, inexpensive, and highly safe method for producing 5-((substituted or unsubstituted)benzyl)-2,2-dimethylcyclopentanone. Another object of the present invention is to provide a novel intermediate compound which can be used in the method.

Solution to Problem

In order to attain the object, a method for producing a cyclopentanone compound in accordance with the present invention is a method for producing a cyclopentanone compound represented by the formula (I)

[Chem. 1]

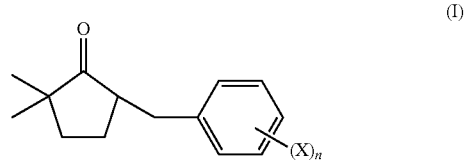

(I)

(wherein X represents a halogen atom, an alkyl group, an alkoxy group, a haloalkyl group, a haloalkoxy group or a phenyl group; n is an integer of 0 to 5; and, when n is 2 or greater, the groups represented by X may be different from each other),
the method includes the steps of:
A) substituting the group represented by Y by a hydrogen atom by allowing a compound represented by the formula (III) or an intermediate compound obtained from the compound represented by the formula (III) to react with a catalyst or a halogenating agent:

[Chem. 2]

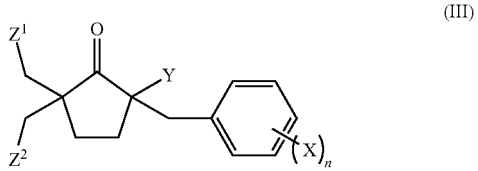

(III)

(wherein X and n are as defined for the formula (I); Y represents an alkoxycarbonyl group or a cyano group; $Z^1$ represents a halogen atom or a substituted sulfonyloxy group; and $Z^2$ represents a hydrogen atom, a halogen atom or a substituted sulfonyloxy group); and B) substituting, by hydrogen atoms, (i) the group or the atom represented by $Z^1$ and (ii) the group or the atom represented by $Z^2$ when $Z^2$ is not a hydrogen atom, by reducing the compound represented by the formula (III) or the intermediate compound obtained from the compound represented by the formula (III).

In order to attain the object, an intermediate compound in accordance with the present invention is an intermediate compound represented by the formula (II):

[Chem. 3]

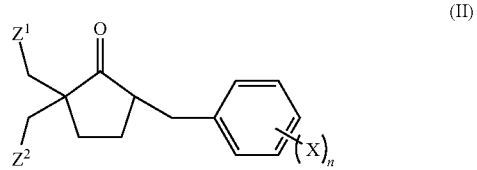

(II)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; $Z^1$ represents a halogen atom or a substituted sulfonyloxy group; and $Z^2$ represents a hydrogen atom, a halogen atom or a substituted sulfonyloxy group).

In order to attain the object, an intermediate compound in accordance with the present invention is an intermediate compound represented by the formula (III):

[Chem. 4]

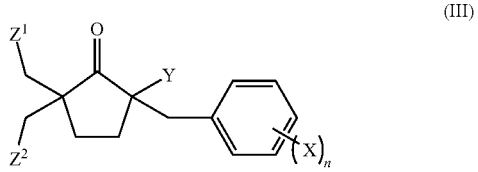

(III)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; Y represents an alkoxycarbonyl group or a cyano group; $Z^1$ represents a halogen atom or a substituted sulfonyloxy group; and $Z^2$ represents a hydrogen atom, a halogen atom or a substituted sulfonyloxy group).

In order to attain the object, an intermediate compound in accordance with the present invention is an intermediate compound represented by the formula (V):

[Chem. 5]

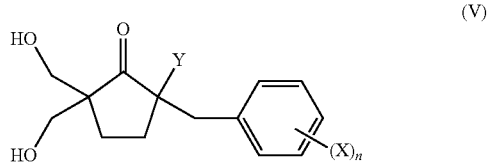

(V)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; and Y represents an alkoxycarbonyl group or a cyano group).

Advantageous Effects of Invention

According to a method for producing a cyclopentanone compound and an intermediate compound in accordance with the present invention, it is possible, without using sodium hydride, methyl bromide or $BF_3$, to produce 5-((substituted or unsubstituted)benzyl)-2,2-dimethylcyclopentanone, which is an intermediate important for the agricultural fungicide "metconazole".

BRIEF DESCRIPTION OF DRAWINGS

FIG. 1 illustrates an entire scheme of specific aspects of a method for producing a cyclopentanone compound in accordance with the present invention. (A) and (B) of FIG. 1 illustrate respective different aspects.

DESCRIPTION OF EMBODIMENTS

The following description will discuss a method for producing a cyclopentanone compound and an intermediate compound in accordance with the present invention.

[Method for Producing 5-((substituted or unsubstituted)benzyl)-2,2-dimethylcyclopentanone]

A method for producing a cyclopentanone compound in accordance with the present invention is a method for producing 5-((substituted or unsubstituted)benzyl)-2,2-dimethylcyclopentanone, which is represented by the formula (I)

[Chem. 6]

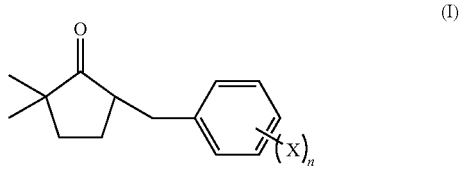

(I)

(wherein X represents a halogen atom, an alkyl group, an alkoxy group, a haloalkyl group, a haloalkoxy group or a phenyl group; n is an integer of 0 to 5; and, when n is 2 or greater, the groups represented by X may be different from each other)

the method includes the steps of:

A) substituting the group represented by Y by a hydrogen atom by allowing a compound represented by the formula (III) or an intermediate compound obtained from the compound represented by the formula (III) to react with a catalyst:

[Chem. 7]

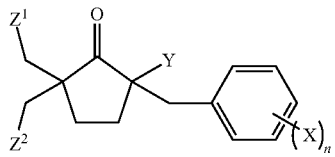

(III)

(wherein X and n are as defined for the formula (I); $Z^1$ represents a halogen atom or a substituted sulfonyloxy group; and $Z^2$ represents a hydrogen atom, a halogen atom or a substituted sulfonyloxy group; Y represents an alkoxycarbonyl group or a cyano group); and B) substituting, by hydrogen atoms, (i) the group or the atom represented by $Z^1$ and (ii) the group or the atom represented by $Z^2$ when $Z^2$ is not a hydrogen atom, by reducing the compound represented by the formula (III) or the intermediate compound obtained from the compound represented by the formula (III).

In the case of a compound represented by the formula (III) in which Y is an alkoxycarbonyl group, the group represented by Y can be substituted by a hydrogen atom in step A with use of a halogenating agent instead of the catalyst.

FIG. 1 illustrates a specific aspect of the method for producing a cyclopentanone compound in accordance with the present invention. Note that, in FIG. 1, Step A1-1 and Step A1-2 are aspects of Step A1 (described later), Step A2-1 and Step A2-2 are aspects of Step A2 (described later), Step B1-1 and Step B1-2 are aspects of Step B1 (described later), and Step B2-1 and Step B2-2 are aspects of Step B2 (described later). Furthermore, in FIG. 1, a compound represented by the formula (IIa) and a compound represented by the formula (IIb) are aspects of a compound represented by the formula (II) (described later).

Note that, in this specification, "the number of carbons p-q" is also represented as "Cp-Cq". For example, in a case where the number of carbons is 1 to 4, it is represented as C1-C4.

In the above formulas, X represents a halogen atom, an alkyl group, an alkoxy group, a haloalkyl group, a haloalkoxy group or a phenyl group. It is preferable that X is a halogen atom, a haloalkyl group or a phenyl group.

Examples of the halogen atom include fluorine atom, chlorine atom, bromine atom, and iodine atom. The halogen atom is preferably fluorine atom, chlorine atom or bromine atom, and particularly preferably chlorine atom.

Examples of the alkyl group include, but are not limited to: C1-C4 alkyl groups such as methyl group, ethyl group, n-propyl group, isopropyl group and n-buthyl group. Of those listed above, methyl group is preferable.

Examples of the alkoxy group include, but are not limited to: C1-C4 alkoxy groups such as methoxy group, ethoxy group, n-propoxy group and t-butoxy group. Of those listed above, methoxy group is preferable.

Examples of the haloalkyl group include, but are not limited to: C1-C4 haloalkyl groups such as chloromethyl group, trifluoromethyl group, difluoromethyl group, trichloromethyl group, 1,1,2,2,2-pentafluoroethyl group and bromomethyl group. Of those listed above, trifluoromethyl group and difluoromethyl group are preferable.

Examples of the haloalkoxy group include, but are not limited to: C1-C4 haloalkoxy groups such as trifluoromethoxy group, difluoromethoxy group, 1,1,2,2,2-pentafluoroethoxy group, and 2,2,2-trifluoroethoxy group. Of those listed above, trifluoromethoxy group is preferable.

n represents an integer of 0 to 5. n is preferably an integer of 0 to 3, and more preferably an integer of 0 to 2. When n is 2 or greater, the groups represented by X may be the same or different from each other.

Y represents an alkoxycarbonyl group or a cyano group. An alkyl moiety in the alkoxycarbonyl group is preferably a C1-C4 alkyl group. Examples of the C1-C4 alkyl group include, but are not limited to: methyl group, ethyl group, isopropyl group, n-propyl group and n-buthyl group. Of these, methyl group and ethyl group are preferable.

$Z^1$ represents a halogen atom or a substituted sulfonyloxy group, and $Z^2$ represents a hydrogen atom, a halogen atom or a substituted sulfonyloxy group.

Examples of the halogen atoms represented by $Z^1$ and $Z^2$ include fluorine atom, chlorine atom, bromine atom and iodine atom. Of these, chlorine atom, bromine atom, and iodine atom are preferable.

Examples of the substituted sulfonyloxy groups represented by $Z^1$ and $Z^2$ include alkylsulfonyloxy group and phenylsulfonyloxy group. A hydrogen atom(s) of an alkyl group in the alkylsulfonyloxy group may be further substituted by a halogen atom. Similarly, a hydrogen atom(s) of a phenyl group in the phenylsulfonyloxy group may be further substituted by a halogen atom, a C1-C4 alkyl group or nitro group.

Examples of the substituted or unsubstituted alkylsulfonyloxy group include, but are not limited to: methanesulfonyloxy group, ethanesulfonyloxy group, propanesulfonyloxy group and trifluoromethanesulfonyloxy group.

Examples of the substituted or unsubstituted phenylsulfonyloxy group include, but are not limited to: phenylsulfonyloxy group, 4-methylphenylsulfonyloxy group (p-toluenesulfonyloxy group), 4-chlorobenzenesulfonyloxy group and o-nitrobenzenesulfonyloxy group.

Each of the substituted sulfonyloxy groups represented by $Z^1$ and $Z^2$ is preferably methanesulfonyloxy group or 4-methylphenylsulfonyloxy group.

In "the step of substituting the group represented by Y by a hydrogen atom" (step A), the intermediate compound as in "allowing a compound represented by the formula (III) or an intermediate compound obtained from the compound represented by the formula (III) to react with a catalyst" is, specifically, a compound represented by the formula (IV):

[Chem. 8]

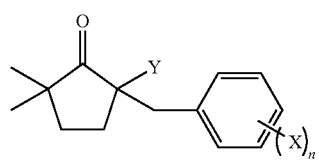

(IV)

(wherein X, n, and Y are as defined for the formula (III)).

The compound represented by the formula (IV) is obtained by, in step B below, reducing the compound represented by the formula (III).

Furthermore, in the case of a compound represented by the formula (IV) in which Y is an alkoxycarbonyl group, the group represented by Y can be substituted by a hydrogen atom in step A with use of a halogenating agent instead of the catalyst.

The compound represented by the formula (III) or the compound represented by the formula (IV) is allowed to react with a catalyst, whereby the group represented by Y is hydrolyzed and decarbonated. In this way, the group represented by Y is substituted by a hydrogen atom.

The catalyst used in step A is preferably an acid catalyst. Examples of the acid catalyst include: inorganic acids such as hydrogen halides (e.g., hydrogen chloride, hydrogen bromide, and hydrogen iodide) and sulfuric acid; organic acids such as formic acid, acetic acid, butyric acid, methanesulfonic acid, trifluoroacetic acid, and p-toluenesulfonic acid; and a mixture of any of those listed above. Of these, hydrogen halides, sulfuric acid, methanesulfonic acid, p-toluenesulfonic acid etc. are preferable. Note that, in step A, in the case where the compound represented by the formula (IV) is allowed to react with a catalyst and thereby the group represented by Y is substituted by a hydrogen atom, a base catalyst can also be used instead of the acid catalyst.

Examples of a solvent used in step A include organic acids such as acetic acid and water. A mixture of any of these can also be suitably used.

The reaction temperature and reaction time can be set appropriately in accordance with the kinds of the solvent and acid catalyst etc. The reaction temperature is, for example, 0° C. to reflux temperature, and preferably room temperature to reflux temperature. The reaction time is, for example, 0.5 hour to several days, and preferably 1 hour to 24 hours.

Furthermore, as described above, in the case of a compound represented by the formula (III) or the formula (IV), in which Y is an alkoxycarbonyl group, the group represented by Y can be substituted by a hydrogen atom in step A with use of a halogenating agent instead of the catalyst.

The halogenating agent is preferably a hydrogen halide or a halide salt. Examples of the hydrogen halide include hydrogen chloride, hydrogen bromide, and hydrogen iodide. Examples of the halide salt include alkali metal halides such as lithium chloride, lithium bromide, lithium iodide, potassium chloride, potassium bromide, potassium iodide, and sodium iodide. With such a halogenating agent, the alkoxycarbonyl group represented by Y is dealkylated and decarbonated, whereby the group represented by Y is substituted by a hydrogen atom.

A solvent used in step A in which a halogenating agent is used is not limited, provided that the solvent is inert. Suitable examples of the solvent include: amides such as N,N-dimethylformamide, N,N-dimethylacetamide, and N-methyl-2-pyrrolidinone; ethers such as dimethoxyethane, tetrahydrofuran and dioxane; and a mixture of any of these solvents and another solvent(s).

The amount of the halogenating agent per mole of the compound represented by the formula (III) or the formula (IV) is, for example, 0.1 mole to 50 moles, and preferably 0.2 mole to 20 moles.

The reaction temperature and reaction time can be set appropriately according to the kinds of the solvent and halogenating agent etc. The reaction temperature is, for example, 0° C. to 250° C., and preferably room temperature to 200° C. The reaction time is, for example, 0.5 hour to several days, and preferably 1 hour to 3 days.

In "the step of substituting, by hydrogen atoms, (i) the group or the atom represented by $Z^1$ and (ii) the group or the atom represented by $Z^2$ when $Z^2$ is not a hydrogen atom" (step B), the intermediate compound as in "reducing the compound represented by the formula (III) or the intermediate compound obtained from the compound represented by the formula (III)" is, specifically, a compound represented by the formula (II):

[Chem. 9]

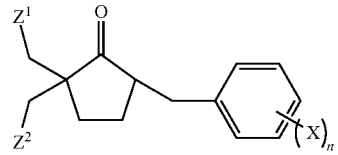

(II)

(wherein X, n, $Z^1$, and $Z^2$ are as defined for the formula (III)).

The compound represented by the formula (II) is obtained, in above step A, by allowing the compound represented by the formula (III) to react with a catalyst or a halogenating agent.

The compound represented by the formula (III) or the compound represented by the formula (II) is reduced, whereby (i) the group or the atom represented by $Z^1$ and (ii) the group or the atom represented by $Z^2$ (when $Z^2$ is not a hydrogen atom) are substituted by hydrogen atoms.

The compound represented by the formula (III) or the compound represented by the formula (II) can be reduced by, for example, allowing the compound represented by the formula (III) or the compound represented by the formula (II) to react with a reducing agent in an inert solvent.

Examples of the reducing agent include: metals such as zinc, iron, aluminum, tin, and Raney nickel; and radical reducing agents such as tributyltin, triphenyltin, phosphinic acid, and phosphinic acid salt. Of these, metals such as zinc are suitable.

The amount of the reducing agent per mole of the compound represented by the formula (III) or the intermediate compound obtained from the compound represented by the formula (III) is, for example, 0.5 mole to 1000 moles, and preferably 0.8 mole to 100 moles.

A solvent used in step B is not limited, provided that the solvent is inert. Examples of the solvent include: ethers such as diethyl ether, dimethoxyethane, tetrahydrofuran, and dioxane; alcohols such as methanol, ethanol, and isopropanol; aromatic hydrocarbons such as benzene, toluene, and xylene; aliphatic hydrocarbons such as petroleum ether, hexane, and methylcyclohexane; and amides such as N,N-dimethylformamide, N,N-dimethylacetamide, and N-methyl-2-pyrrolidinone. Other examples of the solvent include water, acetonitrile, ethyl acetate, acetic acid, pyridine, and dimethyl sulfoxide. Two or more of these solvents may be used in combination. It is advantageous that the reactions in the production method of the present embodiment be performed in a solvent or a mixture of solvents.

Alternatively, the solvent may be a solvent composition composed of solvents which do not form a homogenous layer with each other. In this case, it may be preferable to add a phase transfer catalyst such as a general-use quaternary ammonium salt or crown ether to the reaction system.

In a case where the reducing agent is zinc, a suitable solvent is, for example: acetic acid or a mixture of acetic acid and water; an amide such as N,N-dimethylformamide, N,N-dimethylacetamide or N-methyl-2-pyrrolidinone; an ether such as dimethoxyethane, tetrahydrofuran or dioxane; or a mixture of any of these solvents and another solvent.

The reaction temperature and reaction time can be set appropriately according to the kinds of the solvent and reducing agent etc. The reaction temperature is, for example, 0° C.

to 250° C., and preferably room temperature to 150° C. The reaction time is, for example, 0.5 hour to 5 days, and preferably 1 hour to 2 days.

The order in which step A and step B are performed is not particularly limited. The reaction of step B can be performed after the reaction of step A, or the reaction of step A can be performed after the reaction of step B.

Note here that, in the case where the reaction of step B is performed after the reaction of step A, step A is to obtain the intermediate compound represented by the formula (II) by allowing the compound represented by the above formula (III) to react with a catalyst acid or a halogenating agent, and step B is to obtain the compound represented by the formula (I) by reducing the intermediate compound represented by the formula (II).

That is, in the case where the reaction of step B is performed after the reaction of step A, the production method in accordance with the present invention can be interpreted as a method for producing a cyclopentanone compound, the method including the steps of: (A1) obtaining the intermediate compound represented by the formula (II) by allowing the compound represented by the formula (III) to react with a catalyst acid or a halogenating agent to thereby substitute, by a hydrogen atom, the substituent represented by Y in the compound represented by (III); and (B1) obtaining the compound represented by the formula (I) by reducing the intermediate compound represented by the formula (II), which was obtained in step (A1), to thereby substitute, by hydrogen atoms, (i) the group or the atom represented by $Z^1$ and (ii) the group or the atom represented by $Z^2$ (when $Z^2$ is not a hydrogen atom) in the intermediate compound. A reaction scheme (Reaction scheme 1) in this case is as follows:

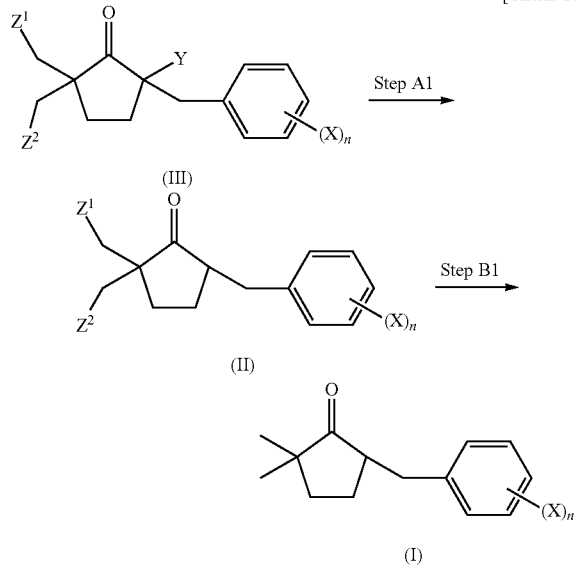

On the other hand, in the case where the reaction of step A is performed after reaction of step B, step B is to obtain the intermediate compound represented by the formula (IV) by reducing the compound represented by the above formula (III), and step A is to obtain the compound represented by the formula (I) by allowing the intermediate compound represented by the formula (IV) to react with a catalyst or a halogenating agent.

That is, in the case where the reaction of step A is performed after the reaction of step B, the production method in accordance with the present invention can be interpreted as a method for producing a cyclopentanone compound, the method including the steps of: (B2) obtaining the intermediate compound represented by the formula (IV) by reducing the compound represented by the formula (III) to thereby substitute, by hydrogen atoms, (i) the group or the atom represented by $Z^1$ and (ii) the group or the atom represented by $Z^2$ (when $Z^2$ is not a hydrogen atom); and (A2) obtaining the compound represented by the formula (I) by allowing the intermediate compound represented by the formula (IV), which was obtained in the step B2, to react with a catalyst or a halogenating agent to thereby substitute, by a hydrogen atom, the substituent represented by Y in the intermediate compound. A reaction scheme (Reaction scheme 2) in this case is as follows:

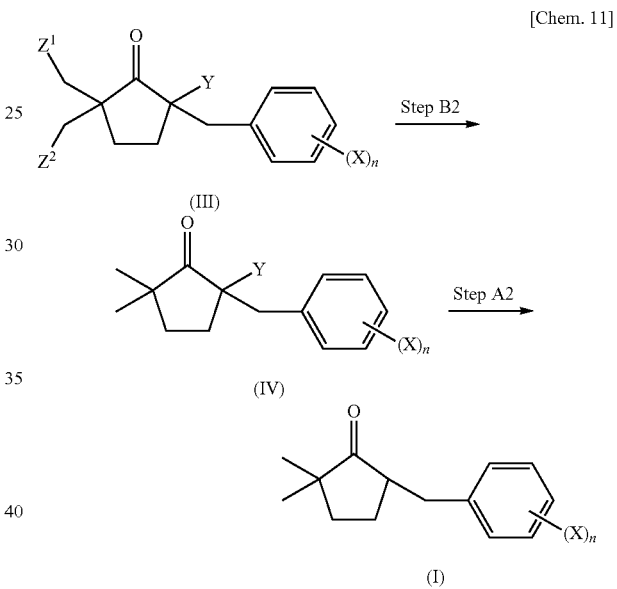

Furthermore, the reaction of step A and the reaction of step B do not have to be performed separately from each other. The reaction of step A and the reaction of step B can be performed concurrently in one reaction system. For example, as described in Production Example 3 of Example 1 (described later), by using the same solvent both in step A and step B, and by adding both (i) an acid catalyst or a halogenating agent and (ii) a reducing agent to the reaction system, it is possible to perform the reaction of step A and the reaction of step B concurrently. This makes it possible to reduce the number of steps. In the reaction system of Production Example 3 of Example 1 (described later), both an acid catalyst and a reducing agent are present. In the reaction system of Production Example 11 of Example 4 (described later), both a halogenating agent and a reducing agent are present.

(Intermediate Compound Production Method 1)

In one aspect of the method for producing a cyclopentanone compound in accordance with the present invention, $Z^2$ in the formula (III) is a substituted sulfonyloxy group or a halogen atom.

A compound represented by the formula (III) in which $Z^2$ is a substituted sulfonyloxy group or a halogen atom, in other words, a compound represented by the formula (IIIa):

[Chem. 12]

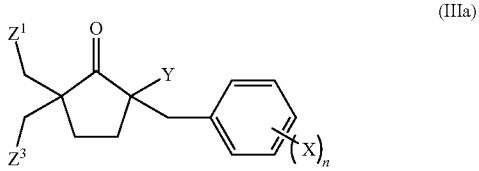

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; Y represents an alkoxycarbonyl group or a cyano group; and $Z^1$ and $Z^3$ each represent a substituted sulfonyloxy group or a halogen atom), is obtained by step C and step D as illustrated in the reaction scheme (Reaction scheme 3) below.

[Chem. 13]

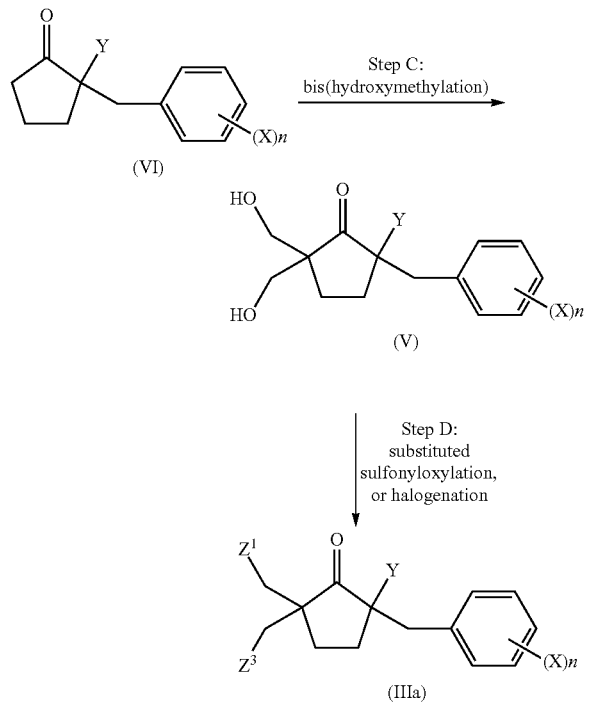

Step C is to obtain, by allowing a compound represented by the formula (VI) (wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; and Y represents an alkoxycarbonyl group or a cyano group) to react with formaldehyde or a formaldehyde derivative, a compound represented by the formula (V) (wherein X, n, and Y are as defined for the formula (VI)). Step D is to obtain the compound represented by the formula (IIIa) by allowing the compound represented by the formula (V) to react with a sulfonyl chloride or a halogenating agent.

Note here that (i) the definitions for the halogen atom and the substituted sulfonyloxy group represented by $Z^3$ and (ii) preferable halogen atoms and preferable substituted sulfonyloxy groups represented by $Z^3$ are identical with those for $Z^2$ in the formula (III).

Furthermore, X, n, and Y in each of the formulas (V) and (VI) are as defined for the formula (III). Similarly, $Z^1$ in the formula (IIIa) is as defined for the formula (III).

Therefore, another aspect of the method for producing a cyclopentanone compound in accordance with the present invention can be a production method further including the steps of: obtaining the compound represented by the formula (V) by allowing the compound represented by the formula (VI) to react with formaldehyde or a formaldehyde derivative; and obtaining the compound represented by the formula (III) in which $Z^2$ is a substituted sulfonyloxy group or a halogen atom by allowing the compound represented by the formula (V) to react with a sulfonyl chloride or a halogenating agent.

In step C, the compound represented by the formula (VI) is allowed to react with formaldehyde or a formaldehyde derivative (hereinafter collectively referred to as "formaldehyde etc.") in the presence of a base, whereby the compound represented by the formula (VI) is subjected to hydroxymethylation. In this way, the compound represented by the formula (V) is obtained.

Examples of the formaldehyde derivative include paraformaldehyde, 1,3,5-trioxane, and formaldehyde dialkyl acetal. In particular, a formaldehyde aqueous solution such as formalin can be suitably used.

The amount of the formaldehyde etc. per mole of the compound represented by the formula (VI) is, for example, 1 mole to 10 moles, and preferably 1.8 moles to 5 moles.

Examples of the base include: inorganic bases such as alkali metal carbonates (e.g., sodium carbonate and potassium carbonate), alkali metal hydroxides (e.g., sodium hydroxide and potassium hydroxide) and hydrogen carbonates (e.g., sodium hydrogen carbonate). Alternatively, an organic base such as triethylamine can also be used. However, the base is not limited to those listed above. In particular, alkali metal carbonates such as potassium carbonate, hydrogen carbonates such as sodium hydrogen carbonate, triethylamine and the like are suitably used.

The amount of the base per mole of the compound represented by the formula (VI) is, for example, 0.1 mole to 10 moles, and preferably 0.2 mole to 3 moles.

A solvent is not particularly limited. Examples of the solvent include: ethers such as diethyl ether, dimethoxyethane, tetrahydrofuran, and dioxane; alcohols such as methanol, ethanol, and isopropanol; aromatic hydrocarbons such as benzene, toluene, and xylene; and amides such as N,N-dimethylformamide, N,N-dimethylacetamide, and N-methyl-2-pyrrolidinone. Other examples include water, acetonitrile, ethyl acetate, and dimethyl sulfoxide. Two or more of these solvents may be used in combination. The reaction can be performed without a solvent depending on conditions, for example, when an organic base such as triethylamine is used.

Alternatively, the solvent may be a solvent composition composed of solvents which do not form a homogenous layer with each other. In this case, it may be preferable to add a phase transfer catalyst such as a general-use quaternary ammonium salt or crown ether to the reaction system.

The reaction temperature is, for example, 0° C. to 150° C., and preferably room temperature to 80° C. The reaction time is, for example, 0.1 hour to several days, and preferably 0.2 hour to 2 days.

Note that the compound represented by the formula (VI) can be produced by a known method.

In step D, the compound represented by the formula (V) is allowed to react with (i) a halogenating agent such as a thionyl halide or (ii) a sulfonyl chloride so that a hydroxy group is substituted by a halogen atom or is converted to a substituted sulfonyloxy group, whereby the compound represented by the formula (IIIa) is obtained.

Examples of the halogenating agent include thionyl halides, phosphorus halides and hydrogen halides. Suitable examples are thionyl halides, and thionyl iodide, thionyl bromide and thionyl chloride. In particular, thionyl chloride is preferably used. When using thionyl chloride, it is more preferable to add a dimethylformamide etc. in order to promote the reaction.

Examples of the sulfonyl chloride include methane sulfonyl chloride, propane sulfonyl chloride, trifluoro methane sulfonyl chloride, benzene sulfonyl chloride, 4-chlorobenzene sulfonyl chloride, p-toluene sulfonyl chloride, and o-nitrobenzene sulfonyl chloride. Of those listed above, p-toluene sulfonyl chloride, methane sulfonyl chloride and the like are preferably used.

The amount of the thionyl halide or sulfonyl chloride per mole of the compound represented by the formula (V) is, for example, 0.5 mole to 10 moles, and preferably 0.8 mole to 3 moles.

Note here that, when a compound having a substituted sulfonyloxy group is produced, although the reaction proceeds without a base in some cases, it is preferable to add a base in order to remove generated hydrogen chloride. In such a case, the amount of the base per mole of the compound represented by the formula (V) is, for example, 0 mole to 10 moles (excluding 0), and preferably 0.5 mole to 5 moles.

The base used here is not particularly limited. Suitable examples of the base include organic bases such as triethylamine, pyridine, 4-dimethylaminopyridine, N,N-dimethylaniline, and N-methylimidazole.

The reaction can take place in solvent-free conditions in some cases. However, in many cases, the reaction is carried out in a solvent. The solvent used here is not particularly limited, provided that the solvent is not involved in the reaction. Examples of the solvent include: aromatic hydrocarbons such as benzene, toluene, and xylene; ethers such as diethyl ether, tetrahydrofuran, dimethoxyethane and dioxane; and amides such as N,N-dimethylformamide, N,N-dimethylacetamide, and N-methyl-2-pyrrolidinone; and a mixture of any of these solvents and another solvent. Particularly suitable are toluene and tetrahydrofuran, dimethoxyethane, N,N-dimethylformamide, N,N-dimethylacetamide, and a mixture of any of these solvents.

The reaction temperature and reaction time can be set appropriately in accordance with the kind of a solvent to be used, whether a sulfonyl chloride or a thionyl halide is used in reaction, the kind of a base to be used and the like. In a case where the reaction is carried out with use of a sulfonyl chloride, the reaction temperature is, for example, −50° C. to 150° C., and preferably 0° C. to 100° C. In a case where the reaction is carried out with use of a thionyl halide, the reaction temperature is, for example, 0° C. to 200° C., and preferably room temperature to 120° C. Furthermore, in the case where the reaction is carried out with use of a sulfonyl chloride, the reaction time is, for example, 0.1 hour to 2 days, and preferably 0.2 hour to 12 hours. In the case where the reaction is carried out with use of a thionyl halide, the reaction time is, for example, 0.1 hour to 2 days, and preferably 0.2 hour to 12 hours.

(Intermediate Compound Production Method 2)

In one aspect of the method for producing a cyclopentanone compound in accordance with the present invention, $Z^2$ in the formula (III) is a hydrogen atom.

A compound represented by the above formula (III) in which $Z^2$ is a hydrogen atom, in other words, a compound represented by the formula (IIIb):

[Chem. 14]

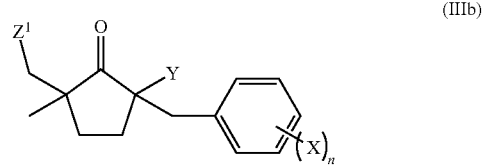

(IIIb)

(wherein X represents a halogen atom, an alkyl group, an alkoxy group, a haloalkyl group, a haloalkoxy group or a phenyl group; n is an integer of 0 to 5; when n is 2 or greater, the groups represented by X may be identical with or different from each other; Y represents an alkoxycarbonyl group or a cyano group; and $Z^1$ represents a substituted sulfonyloxy group or a halogen atom), is obtained by step E and step F, as illustrated in a reaction scheme (Reaction scheme 4) below.

(Reaction scheme 4)

[Chem. 15]

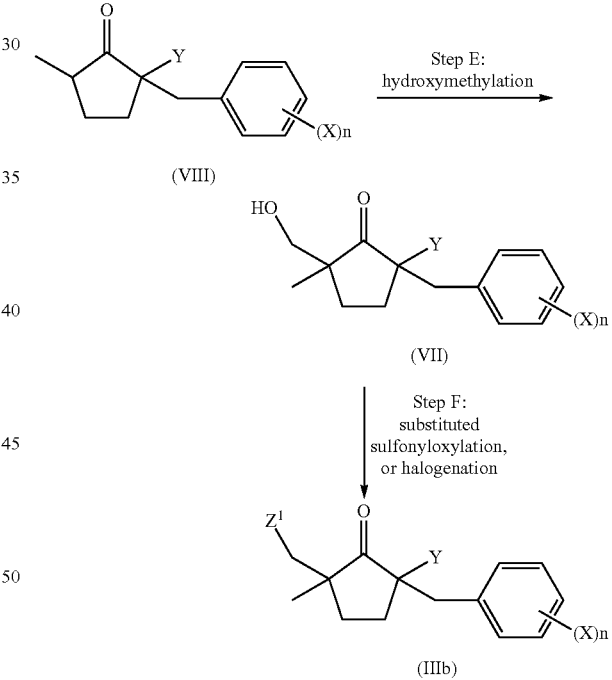

Step E is to obtain a compound represented by the formula (VII) (wherein X, n, and Y are as defined for the formula (VIII)) by allowing a compound represented by the formula (VIII) (wherein X represents a halogen atom, an alkyl group, an alkoxy group, a haloalkyl group, a haloalkoxy group or a phenyl group; n is an integer of 0 to 5; when n is 2 or greater, the groups represented by X may be identical with or different from each other; and Y represents an alkoxycarbonyl group or a cyano group) to react with formaldehyde or a formaldehyde derivative.

Step F is to obtain a compound represented by the formula (IIIb) (wherein $Z^1$ is as defined for the formula (III)) by allowing the compound represented by the formula (VII) to react with a sulfonyl chloride or a halogenating agent.

Therefore, a further aspect of the method for producing a cyclopentanone compound in accordance with the present invention can be a production method further including the steps of: obtaining the compound represented by the formula (VII) by allowing the compound represented by the formula (VIII) to react with formaldehyde or a formaldehyde derivative; and obtaining the compound represented by the formula (III) in which $Z^2$ is a hydrogen atom by allowing the compound represented by the formula (VII) to react with a sulfonyl chloride or a halogenating agent.

The reaction in step E is performed under the same conditions as the reaction in step C, except that the compound represented by the formula (VIII) is used as a starting material instead of the compound represented by the formula (VI). Furthermore, compounds which can be used in the reaction in step E are the same as those which can be used in the reaction in step C.

Note that the compound represented by the formula (VIII) can be produced by a known method (e.g., a method described in the aforesaid Patent Literature 1).

Similarly, the reaction in step F is performed under the same conditions as the reaction in step D, except that the compound represented by the formula (VII) is used as a starting material instead of the compound represented by the formula (V). Furthermore, compounds which can be used in the reaction in step F are the same as those which can be used in the reaction in step D.

Alternatively, it is also possible to produce a compound represented by the formula (IIId) (which is a compound represented by the formula (III) in which $Z^1$ is a halogen atom and $Z^2$ is a halogen atom or a hydrogen atom), by subjecting, in a solvent, a compound represented by the formula (IIIc) (which is a compound represented by the formula (III) in which $Z^1$ is a substituted sulfonyloxy group and $Z^2$ is a substituted sulfonyloxy group or a hydrogen atom) to substitution using a halide salt etc. (see Reaction scheme 5 below).

(Reaction scheme 5)

[Chem. 16]

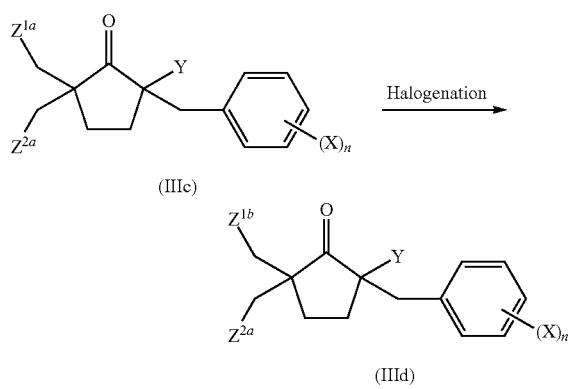

(in the formulas (IIIc) and (IIId), X, Y, and n are as defined for the formula (III); $Z^{1a}$ represents a substituted sulfonyloxy group; $Z^{2a}$ represents a substituted sulfonyloxy group or a hydrogen atom; $Z^{1b}$ represents a halogen atom; and $Z^{2b}$ represents a halogen atom or a hydrogen atom).

Similarly, it is also possible to produce a compound represented by the formula (IId) (which is a compound represented by the formula (II) in which $Z^1$ is a halogen atom and $Z^2$ is a halogen atom or a hydrogen atom), by substituting, in a solvent, a compound represented by the formula (IIc) (which is a compound represented by the formula (II) in which $Z^1$ is a substituted sulfonyloxy group and $Z^2$ is a substituted sulfonyloxy group or a hydrogen atom) to substitution using a halide salt etc. (see Reaction scheme 6 below).

(Reaction Scheme 6)

[Chem. 17]

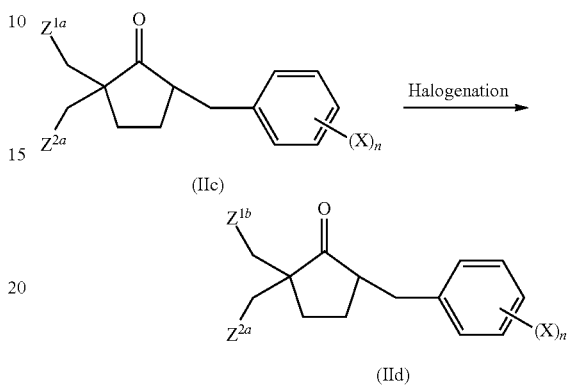

(in the formulas (IIc) and (IId), X, and n are as defined for the formula (II); $Z^{1a}$ represents a substituted sulfonyloxy group; $Z^{2a}$ represents a substituted sulfonyloxy group or a hydrogen atom; $Z^{1b}$ represents a halogen atom; and $Z^{2b}$ represents a halogen atom or a hydrogen atom).

The reactions are usually carried out by mixing, in a solvent, the compound represented by the formula (IIIc) or the formula (IIc) with a halide salt(s) such as potassium fluoride, cesium fluoride, lithium chloride, potassium chloride, lithium bromide, magnesium bromide and/or sodium iodide.

The amount of the halide salt(s) per mole of the compound represented by the formula (IIIc) or the formula (IIc) is, for example, 0.1 mole to 100 moles, and preferably 0.8 mole to 20 moles. The reaction temperature is, for example, 0° C. to 250° C., and preferably room temperature to 200° C. The reaction time is, for example, 0.1 hour to several days, and preferably 0.2 hour to 2 days.

A solvent used here is not particularly limited, provided that the solvent is not involved in the reaction. Preferable examples of the solvent are amides such as N,N-dimethylformamide, N,N-dimethylacetamide, and N-methyl-2-pyrrolidinone.

Note that, in the production method in accordance with the present invention, unless otherwise specified, the following solvents are usable provided that the solvents are not involved in the reaction: aromatic hydrocarbons such as benzene, toluene, and xylene; halogenated hydrocarbons such as dichloromethane, chloroform, and dichloroethane; aliphatic hydrocarbons such as petroleum ether, hexane, and methylcyclohexane; amides such as N,N-dimethylformamide, N,N-dimethylacetamide, and N-methyl-2-pyrrolidinone; ethers such as diethyl ether, tetrahydrofuran, dimethoxyethane, and dioxane; alcohols such as methanol and ethanol; water; carbon disulfide; acetonitrile; ethyl acetate; pyridine; dimethylsulfoxide and the like.

Two or more of these solvents may be used in combination. It is advantageous that the reactions in the production method in accordance with the present invention be carried out in a solvent or in a solvent mixture.

Alternatively, the solvent may be a solvent composition composed of solvents which do not form a homogenous layer with each other. In this case, it may be preferable to add a phase transfer catalyst such as a general-use quaternary ammonium salt or crown ether to the reaction system.

As has been described, according to the method for producing a cyclopentanone compound in accordance with the present invention, it is possible to produce 5-((substituted or unsubstituted)benzyl)-2,2-dimethylcyclopentanone which is an important intermediate for an agricultural fungicide "metconazole", without using sodium hydride, methyl bromide or $BF_3$. That is, by the method for producing a cyclopentanone compound in accordance with the present invention, it is possible to produce 5-((substituted or unsubstituted)benzyl)-2,2-dimethylcyclopentanone more inexpensively and safely than conventional production methods. Therefore, it is possible to provide a practical industrial method for producing 5-((substituted or unsubstituted)benzyl)-2,2-dimethylcyclopentanone and metconazole.

(Intermediate Compound)

Intermediate compounds represented by the formula (II) (an intermediate compound represented by the formula (IIa) and an intermediate compound represented by the formula (IIb) in FIG. 1), intermediate compounds represented by the formula (III) (an intermediate compound represented by the formula (IIIa) and an intermediate compound represented by the formula (IIIb)), and an intermediate compound represented by the formula (V) are all compounds which are suitable for uses in the aforesaid method for producing a cyclopentanone compound. That is, these intermediate compounds are also encompassed in the scope of the present invention.

The following description provides Examples to further specifically explain the embodiments of the present invention. It is needless to say that the present invention is not limited to these Examples, and details thereof can take various aspects. Furthermore, the present invention is not limited to the description of the embodiments above, but may be altered within the scope of the claims. An embodiment based on a proper combination of disclosed technical means is encompassed in the technical scope of the present invention. Furthermore, all the literatures cited in this specification are of assistance as references in this specification.

EXAMPLES

Example 1

Production Example 1

Synthesis of 1-(4-chlorobenzyl)-3-hydroxymethyl-3-methyl-2-oxocyclopentanecarboxylic acid methyl ester (Compound VII-1)

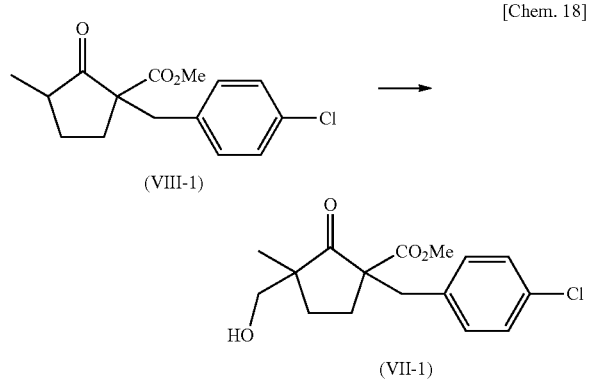

A 37% formaldehyde aqueous solution (0.90 ml) and potassium carbonate (2.00 mmol) were added to 1-(4-chlorobenzyl)-3-methyl-2-oxocyclopentanecarboxylic acid methyl ester (Compound VIII-1) (4.00 mmol), and the resultant mixture was stirred at room temperature for 4 hours. After the reaction, water was added to the resultant reaction solution, and the solution was extracted with ethyl acetate. The organic layer was washed with saturated brine, and thereafter dried over anhydrous sodium sulfate. The solvent was distilled off, and a residue was purified with the use of a silica gel column. In this way, Compound VII-1 in the form of two isomers (isomer VII-1a and isomer VII-1b) was obtained. Note that Compound VIII-1 was synthesized in accordance with a method described in Patent Literature 1.

Isomer VII-1a
  Yield: 18%
Isomer VII-1b
  Yield: 76%

Production Example 2

Synthesis of 1-(4-chlorobenzyl)-3-chloromethyl-3-methyl-2-oxocyclopentanecarboxylic acid methyl ester (Compound III-1)

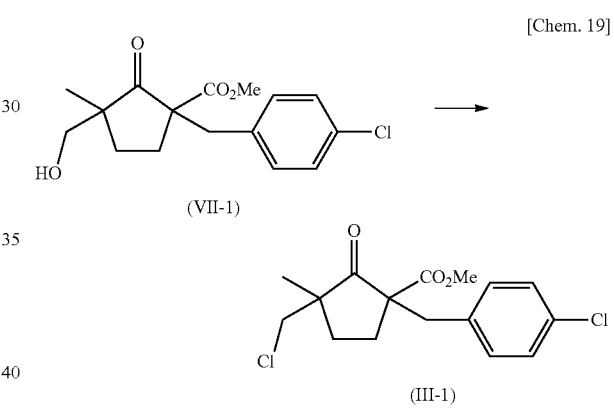

Compound VII-1 (9.65 mmol) was dissolved in toluene (10 ml), and thionyl chloride (23.0 mmol) and dimethylformamide (0.05 ml) were added. The resultant mixture was allowed to react at 90° C. for 9 hours. The resultant reaction solution was concentrated to obtain a crude desired substance, and the crude desired substance was purified with the use of a silica gel column. In this way, Compound III-1 in the form of two isomers (isomer VIII-1a and isomer III-1b) was obtained. Note that the resultant product was a mixture of two kinds of diastereomers.

The following are the results of analysis.

Yield: 84%

Isomer III-1a $^1$H-NMR (400 MHz, $CDCl_3$) δ:

0.78 (3H, s), 1.51-1.61 (1H, m), 1.75-1.90 (1H, m), 2.15-2.27 (1H, m), 2.36-2.48 (1H, m), 3.15 (2H, s), 3.42 (1H, d, J=11.0 Hz), 3.61 (1H, d, J=11.0 Hz), 3.72 (3H, s), 7.00-7.06 (2H, m), 7.20-7.26 (2H, m).

Isomer III-1b $^1$H-NMR (400 MHz, $CDCl_3$) δ:

1.18 (3H, s), 1.75-1.90 (1H, m), 1.90-2.01 (1H, m), 2.01-2.10 (1H, m), 2.36-2.48 (1H, m), 2.97 (1H, d, J=14.0 Hz), 3.23 (1H, d, J=14.0 Hz), 3.29 (1H, d, J=11.0 Hz), 3.33 (1H, d, J=11.0 Hz), 3.73 (3H, s), 7.06-7.11 (2H, m), 7.20-7.26 (2H, m).

Production Example 3

Synthesis 1 of 5-(4-chlorobenzyl)-2,2-dimethylcyclopentanone (Compound I-1)

[Chem. 20]

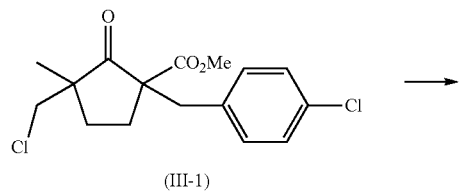
(III-1)

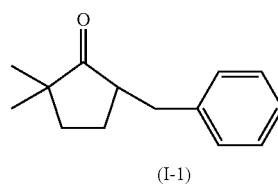
(I-1)

Compound III-1 (0.61 mmol) was dissolved in a 47% hydrobromic acid aqueous solution (1 ml) and acetic acid (1 ml). To the solution, zinc (6.1 mmol) was added. The resultant mixture was reacted at 110° C. for 12 hours. Then, acetic acid (1 ml), a 47% hydrobromic acid aqueous solution (1 ml), and zinc (3.06 mmol) were further added to the resultant reaction solution, and the solution was stirred for another 11 hours. After the reaction, water was added to the resultant reaction solution, and the reaction solution was extracted with ethyl acetate. The organic layer was washed with a saturated sodium bicarbonate solution and saturated brine, and thereafter dried over anhydrous sodium sulfate. The solvent was distilled off, and thereafter the residue was purified with the use of a silica gel column. In this way, Compound I-1 was obtained.

Yield: 52%

The properties and $^1$H-NMR Spectrum data of Compound I-1 obtained above were well in agreement with data described in Patent Literature 1.

Example 2

Production Example 4

Synthesis of 5-(4-chlorobenzyl)-2-chloromethyl-2-methylcyclopentanone (Compound II-1)

[Chem. 21]

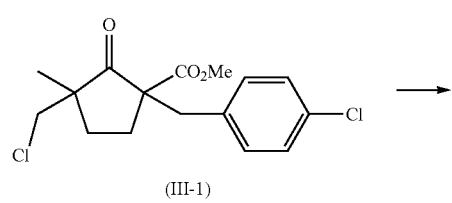
(III-1)

-continued

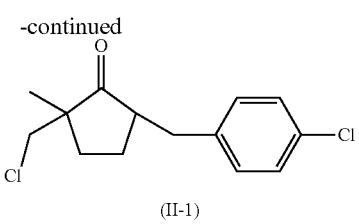
(II-1)

p-toluenesulfonic acid monohydrate (47.3 mmol) and water (212 mmol) were added to Compound III-1 (42.5 mmol), and the mixture was stirred at 110° C. for 14 hours. Water was added to the resultant reaction solution, and the resultant reaction solution was extracted with ethyl acetate. The organic layer was washed with saturated brine, and thereafter dried over anhydrous sodium sulfate. The solvent was distilled off, and the residue was purified with the use of a silica gel column. In this way, Compound II-1 was obtained as a mixture of two isomers.

Yield: 90%

$^1$H-NMR (400 MHz, CDCl$_3$) δ:

0.93 (1.8H, s), 1.14 (1.2H, s) 1.42-1.75 (2H, m), 1.90-2.34 (2H, m), 2.35-2.48 (0.6H, m), 2.50-2.70 (1.4H, m), 2.90-3.10 (0.4H, m), 3.10 (0.6H, dd, J=14.0 Hz), 3.33 (0.4H, d, J=10.9 Hz), 3.41 (0.6H, d, J=10.8 Hz), 3.47 (0.4H, d, J=10.9 Hz), 3.67 (0.6H, d, J=10.8 Hz), 7.00-7.13 (2H, m), 7.22-7.30 (2H, m).

Production Example 5

Synthesis 2 of 5-(4-chlorobenzyl)-2,2-dimethylcyclopentanone (Compound I-1)

[Chem. 22]

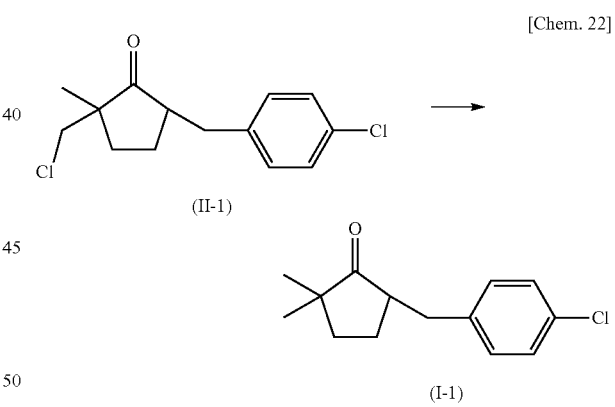

Compound II-1 (1.48 mmol) was dissolved in acetic acid (4 ml). To the solution, a 2N hydrochloric acid aqueous solution (1.5 ml), water (2.5 ml), and zinc (29.5 ml) were added, and the mixture was allowed to react for 5 hours under reflux. After that, a 2N hydrochloric acid aqueous solution (1.5 ml) was added, and the resultant mixture was allowed to react for another 12 hours under reflux. After the reaction, water was added to the resultant reaction solution, and the reaction solution was extracted with ethyl acetate. The organic layer was washed with a saturated sodium bicarbonate solution and saturated brine, and thereafter dried over anhydrous sodium sulfate. The solvent was distilled off, and thereafter the residue was purified with the use of a silica gel column. In this way, Compound I-1 was obtained.

Yield: 48%

Example 3

Production Example 6

Synthesis of 1-(4-chlorobenzyl)-3,3-bis(hydroxymethyl)-2-oxocyclopentanecarboxylic acid methyl ester (Compound V-1)

[Chem. 23]

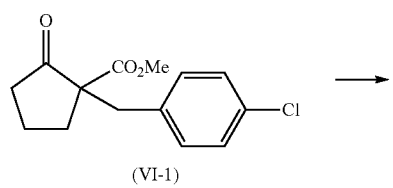

(VI-1)

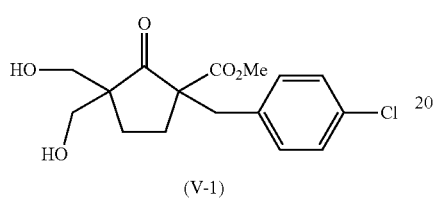

(V-1)

Tetrahydrofuran (0.72 ml), a 37% formaldehyde aqueous solution (0.242 ml), and potassium carbonate (0.50 mmol) were added to 1-(4-chlorobenzyl)-2-oxocyclopentanecarboxylic acid methyl ester (Compound VI-1) (1.0 mmol), and the mixture was allowed to react at room temperature for 5 hours. Water was added to the resultant reaction solution, and the resultant reaction solution was extracted with ethyl acetate. The organic layer was washed with saturated brine, and thereafter dried over anhydrous sodium sulfate. The solvent was distilled off, and the residue was purified with the use of a silica gel column. In this way, Compound V-1 was obtained.

Yield: 94%

$^1$H-NMR (400 MHz, CDCl$_3$) δ:
1.72-1.80 (1H, m), 1.91-2.01 (3H, m), 2.15-2.19 (1H, m), 2.40-2.45 (1H, m), 3.10 (1H, d, J=13.8 Hz), 3.17 (1H, d, J=13.8 Hz), 3.36 (1H, dd, J=11.0, 7.3 Hz), 3.43 (1H, dd, J=11.0, 4.2 Hz), 3.69-3.75 (2H, m), 3.73 (3H, s), 7.05 (2H, d, J=8.4 Hz), 7.24 (2H, d, J=8.4 Hz).

Production Example 7

Synthesis of 1-(4-chlorobenzyl)-3,3-bis(chloromethyl)-2-oxocyclopentanecarboxylic acid methyl ester (Compound III-2)

[Chem. 24]

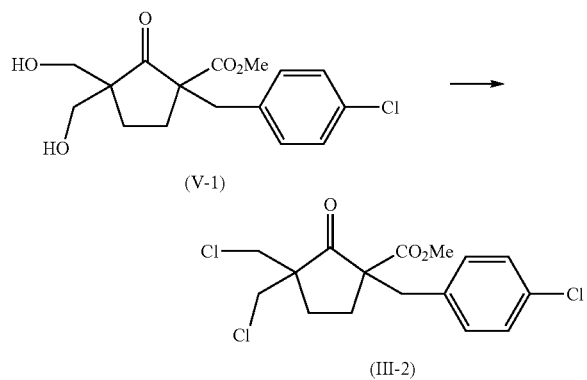

Toluene (20 ml), thionyl chloride (16.5 mmol), and dimethylformamide (0.05 ml) were added to Compound V-1 (6.4 mmol), and the mixture was allowed to react at 100° C. for 4 hours. The resultant reaction solution was concentrated to obtain a crude desired substance, and the crude desired substance was purified with the use of a silica gel column. In this way, Compound III-2 was obtained.

Yield: 54%

$^1$H-NMR (400 MHz, CDCl$_3$) δ:
1.82-2.07 (2H, m), 2.14-2.28 (1H, m), 2.37-2.53 (1H, m), 3.08 (1H, d, J=13.9 Hz), 3.21 (1H, d, J=13.9 Hz), 3.34 (1H, d, J=11.4 Hz), 3.38 (1H, d, J=11.4 Hz), 3.61 (1H, d, J=11.4 Hz), 3.64 (1H, d, J=11.4 Hz), 7.20-7.10 (2H, m), 7.22-7.28 (2H, m).

Production Example 8

Synthesis of 5-(4-chlorobenzyl)-2,2-bis(chloromethyl)cyclopentanone (Compound II-2)

[Chem. 25]

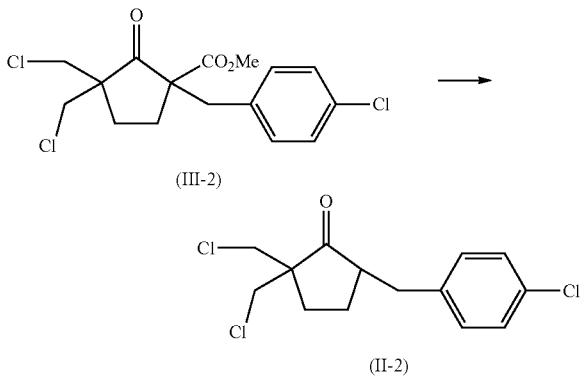

Concentrated hydrochloric acid (30 ml) and acetic acid (30 ml) were added to Compound III-2 (19.1 mmol), and the mixture was stirred at 100° C. for 18 hours. Water was added to the resultant reaction solution, and the resultant reaction solution was extracted with toluene. The organic layer was washed with a saturated sodium bicarbonate solution and saturated brine, and thereafter dried over anhydrous sodium sulfate. The solvent was distilled off, and the residue was purified with the use of a silica gel column. In this way, Compound II-2 was obtained.

Yield: 80%

$^1$H-NMR (400 MHz, CDCl$_3$) δ:
1.50-1.68 (1H, m), 2.02-2.22 (3H, m), 2.48-2.60 (1H, m), 2.64 (1H, dd, J=13.8, 8.6 Hz), 3.08 (1H, dd, J=13.8, 4.3 Hz), 3.41 (2H, s), 3.61 (1H, d, J=11.0 Hz), 3.66 (1H, d, J=11.0 Hz), 7.05-7.13 (2H, m), 7.22-7.30 (2H, m).

Production Example 9

Synthesis 3 of 5-(4-chlorobenzyl)-2,2-dimethylcyclopentanone (Compound 1-1)

[Chem. 26]

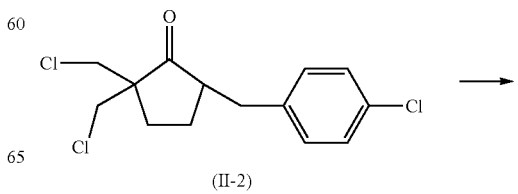

(II-2)

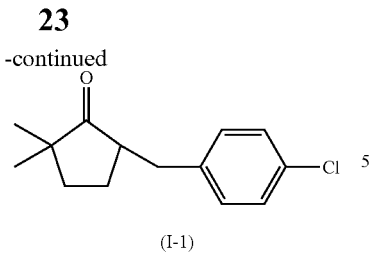

(I-1)

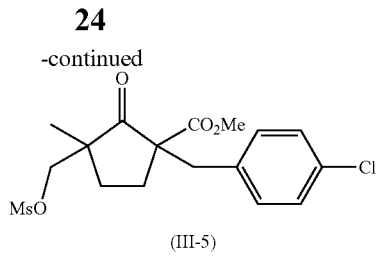

(III-5)

Compound II-2 (0.55 mmol) was dissolved in water (2 ml) and acetic acid (2 ml). To the solution, zinc (5.5 mmol) and acetyl chloride (1.12 mmol) were added, and the mixture was allowed to react at 110° C. for 14 hours. Then, zinc (5.5 mmol) and acetyl chloride (1.12 mmol) were added to the resultant reaction solution, and the reaction solution was stirred for another 9 hours. After the reaction, water was added to the resultant reaction solution, and the resultant reaction solution was extracted with ethyl acetate. The organic layer was washed with a saturated sodium bicarbonate solution and saturated brine, and thereafter dried over anhydrous sodium sulfate. The solvent was distilled off, and the residue was purified with the use of a silica gel column. In this way, Compound I-1 was obtained.

Yield: 49%

Example 4

Production Example 10

Synthesis of 1-(4-chlorobenzyl)-3-methanesulfonyloxymethyl-3-methyl-2-oxocyclopentanecarboxylic acid methyl ester (Compound III-5)

[Chem. 27]

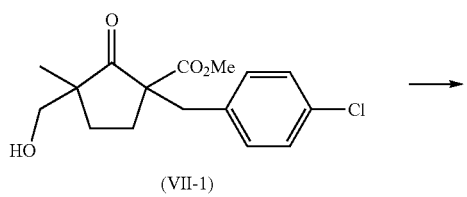

(VII-1)

Compound VII-1 (3.22 mmol) obtained in Production Example 1 was dissolved in methylene chloride (20 ml). To the solution, triethylamine (4.83 mmol) and methane sulfonyl chloride (4.19 mmol) were added, and the mixture was stirred at room temperature for 1.5 hours. After the reaction, water was added to the resultant reaction solution, and the resultant reaction solution was extracted with ethyl acetate. The organic layer was washed with a sodium hydrogen carbonate aqueous solution and saturated brine, and dried over anhydrous sodium sulfate. The solvent was distilled off, and a residue was purified by silica gel column chromatography. In this way, Compound III-5 was obtained as a mixture of two isomers.

Yield: 91%

Isomer III-5a $^1$H-NMR (CDCl$_3$) δ=

0.72 (3H, s), 1.55-1.65 (1H, m), 1.82-1.90 (1H, m), 2.17-2.26 (1H, m), 2.38-2.45 (1H, m), 2.95 (3H, s), 3.15 (2H, s), 3.73 (3H, s), 4.01 (1H, d, J=9.7 Hz), 4.18 (1H, d, J=9.7 Hz), 7.03 (2H, d, J=8.5 Hz), 7.23 (2H, d, J=8.5 Hz).

Isomer III-5b $^1$H-NMR (CDCl$_3$) δ=

1.13 (3H, s), 1.80-1.91 (1H, m), 1.93-2.09 (2H, m), 2.38-2.48 (1H, m), 2.91 (1H, d, J=13.9 Hz), 2.92 (3H, s), 3.24 (1H, d, J=13.9 Hz), 3.74 (3H, s), 3.98 (2H, s), 7.09 (2H, d, J=8.5 Hz), 7.23 (2H, d, J=8.5 Hz).

Production Example 11

Synthesis of 1-(4-chlorobenzyl)-3,3-dimethyl-2-oxocyclopentanecarboxylic acid methyl ester (Compound IV-1)

[Chem. 28]

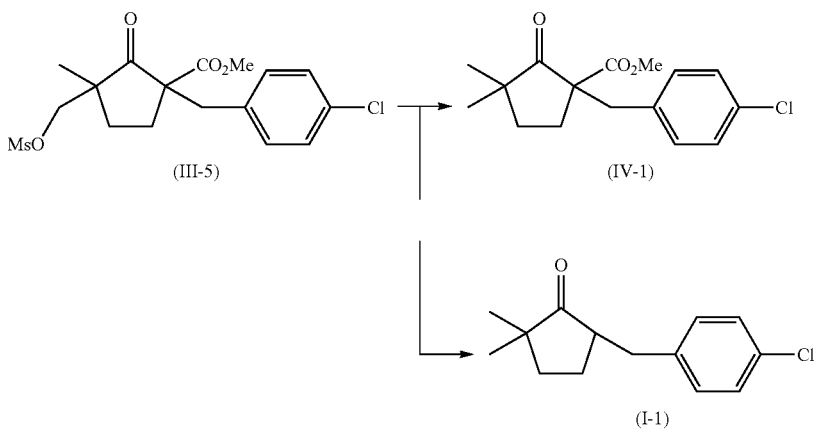

Compound III-5 (5.14 mmol), sodium iodide (5.14 mmol), and zinc (51.4 mmol) were mixed with DMF (4 ml), and thereafter a 4N hydrogen chloride DMF solution (1.3 ml) was added to the mixture. The mixture was heated to 105° C. and stirred for 12 hours. Then, sodium iodide (5.14 mmol) and a 4N hydrogen chloride DMF solution (0.7 ml) were added to the mixture, and the mixture was allowed to react for another 11 hours. Then, zinc (25.7 mmol) and a 4N hydrogen chloride DMF solution (0.7 ml) were added to the mixture, and the mixture was allowed to react for another 15 hours. A sodium bicarbonate solution and ethyl acetate were added to the resultant reaction solution, and the resultant reaction solution was filtered and then partitioned. The organic layer was washed with saturated brine, and thereafter dried over anhydrous sodium sulfate. The solvent was distilled off, and the residue was purified with the use of a silica gel column. In this way, Compound IV-1 and Compound I-1 were obtained.

Compound IV-1
Yield: 51%
Compound I-1
Yield: 17%

The properties and $^1$H-NMR Spectrum data of Compound IV-1 and Compound I-1 obtained in the present Production Example were well in agreement with data described in Patent Literature 1.

Example 5

Production Example 12

Synthesis 4 of 5-(4-chlorobenzyl)-2,2-dimethyl cyclopentanone (Compound I-1)

[Chem. 29]

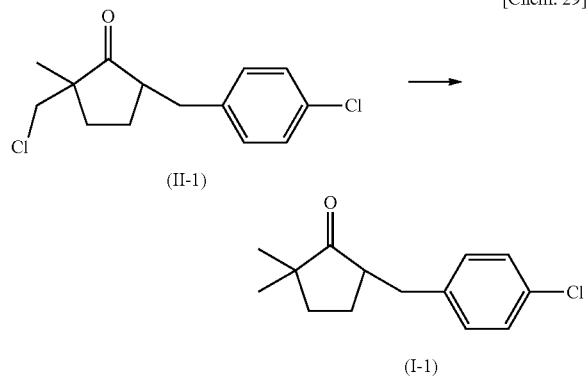

Compound II-1 (3.69 mmol), sodium iodide (4.07 mmol), and zinc (36.7 mmol) were mixed with DMF (3 ml). To the mixture, a 4N hydrogen chloride DMF solution (1.0 ml) was added, and the mixture was heated to 105° C. and stirred for 11 hours. Then, a 4N hydrogen chloride DMF solution (1.0 ml) was added to the mixture, and the mixture was allowed to react for another 10 hours. Then, zinc (18.4 mmol) and a 4N hydrogen chloride DMF solution (1.0 ml) were added to the mixture, and the mixture was allowed to react for another 20 hours. A sodium bicarbonate solution and ethyl acetate were added to the resultant reaction solution, the resultant reaction solution was filtered, and then partitioned. The organic layer was washed with saturated brine, and thereafter dried over anhydrous sodium sulfate. The solvent was distilled off, and the residue was purified with the use of a silica gel column. In this way, Compound I-1 was obtained.

Yield: 86%

The properties and $^1$H-NMR Spectrum data of Compound I-1 obtained in the present Production Example were well in agreement with data described in Patent Literature 1.

Note that compounds represented by the formula (II) can also be produced by the methods described in Reference Production Examples below.

Reference Production Example 1

Synthesis of 5-(4-chlorobenzyl)-2,2-bis(methanesulfonyloxymethyl) cyclopentanone (Compound II-3)

(1) Synthesis of Intermediate "1-(4-chlorobenzyl)-3,3-bis(methanesulfonyloxymethyl)-2-oxocyclopentanecarboxylic acid methyl ester" (Compound III-3)

[Chem. 30]

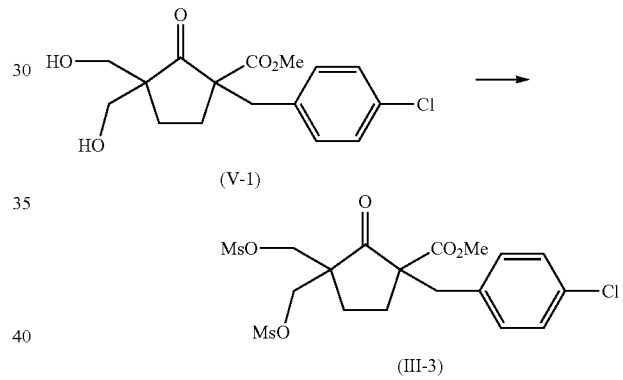

Toluene (100 ml), N,N-dimethylacetamide (10 ml), and triethylamine (62.0 mmol) were added to Compound V-1 (24.5 mmol). After that, to the mixture, methane sulfonyl chloride (50.4 mmol) was added, and the mixture was stirred for 30 minutes while cooling with ice. After that, the ice bath was removed, and the mixture was allowed to react at room temperature for 1 hour. Ethyl acetate was added to the resultant reaction solution, and the mixture was washed with a 1N hydrochloric acid aqueous solution, water, a saturated sodium bicarbonate solution and saturated brine. The aqueous layer was extracted with chloroform. Then, the organic layer was dried over anhydrous sodium sulfate and concentrated, and thereafter the concentrate thus obtained was washed with a solvent (a mixture of diethyl ether and hexane). In this way, Compound III-3, which was a desired substance, was obtained.

Yield: 94%

$^1$H-NMR (400 MHz, CDCl$_3$) δ:

1.98-2.00 (2H, m), 2.07-2.16 (1H, m), 2.46-2.50 (1H, m), 2.95 (3H, s), 3.00 (3H, s), 3.06 (1H, d, J=14.0 Hz), 3.22 (1H, d, J=14.0 Hz), 3.75 (3H, s), 3.86 (1H, d, J=10.0 Hz), 3.98 (1H, d, J=10.0 Hz), 4.21 (2H, s), 7.00-7.10 (2H, m), 7.20-7.30 (2H, m).

(2) Synthesis of 5-(4-chlorobenzyl)-2,2-bis(methane-sulfonyloxymethyl) cyclopentanone (Compound II-3)

[Chem. 31]

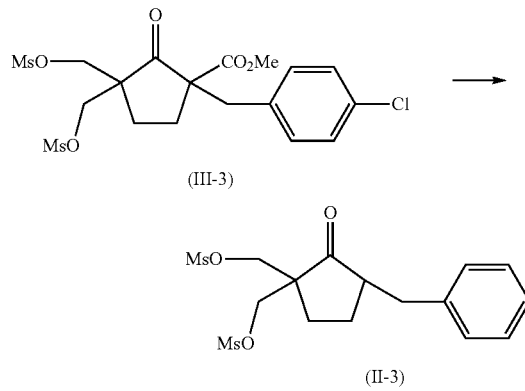

Methanesulfonic acid (14.42 g) and water (6.75 ml) were added to Compound III-3 (36.0 g), and the mixture was allowed to react at 100° C. for 7 hours. Water was added to the resultant reaction solution, and the resultant mixture was neutralized with sodium carbonate. After that, the mixture was extracted with toluene. An organic layer was washed with saturated brine, and thereafter dried over anhydrous sodium sulfate and concentrated. The resultant concentrate was purified with the use of a silica gel column. In this way, Compound II-3, which was a desired substance, was obtained.

Yield: 41%

$^1$H-NMR (400 MHz, CDCl$_3$) δ:

1.62-1.70 (1H, m), 2.01-2.18 (3H, m), 2.55-2.59 (1H, m), 2.62 (1H, dd, J=13.2, 8.4 Hz), 2.99 (3H, s), 3.02 (3H, s), 3.08 (1H, dd, J=13.2, 3.8 Hz), 4.07 (2H, s), 4.21 (1H, d, J=10.0 Hz), 4.21 (1H, d, J=10.0 Hz), 7.05-7.12 (2H, m), 7.23-7.31 (2H, m).

Reference Production Example 2

Synthesis of 5-(4-chlorobenzyl)-2,2-bis(p-toluene-sulfonyloxymethyl)cyclopentanone (Compound II-4)

(1) Synthesis of intermediate "1-(4-chlorobenzyl)-3,3-bis(p-toluenesulfonyloxymethyl)-2-oxocyclopen-tanecarboxylic acid methyl ester" (Compound III-4)

[Chem. 32]

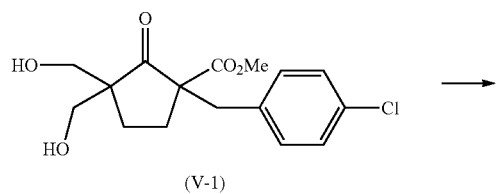

-continued

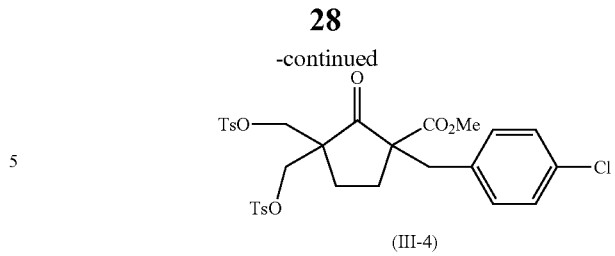

Compound V-1 (15.3 mmol) was suspended in a mixture of toluene (60 ml) and dichloromethane (20 ml). Triethylamine (45.9 mmol), p-toluenesulfonyl chloride (38.2 mmol), and N-methyl imidazole (23.8 mmol) were added to the suspension, and the resulting mixture was allowed to react at room temperature for 18 hours. After that, p-toluenesulfonyl chloride (3.82 mmol) was further added to the mixture, and the mixture was allowed to react for 2 days. Toluene was added to the resultant reaction solution, and the mixture was washed with water, a 2N hydrochloric acid aqueous solution, a saturated sodium bicarbonate solution and saturated brine. The organic layer was dried over anhydrous sodium sulfate, and concentrated. In this way, Compound III-4 was obtained as a crude desired substance.

Crude yield: 77%

(2) Synthesis of 5-(4-chlorobenzyl)-2,2-bis(p-toluenesulfonyloxymethyl) cyclopentanone (Compound II-4)

[Chem. 33]

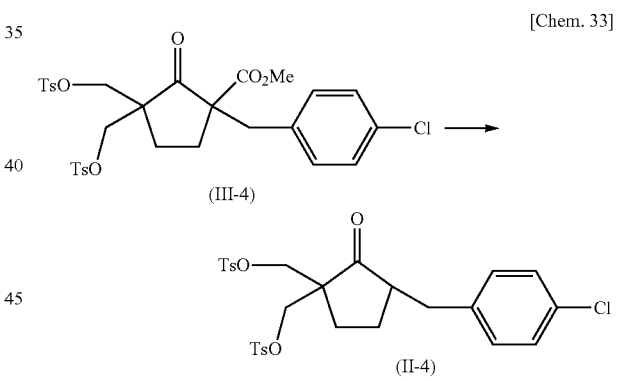

p-toluenesulfonic acid monohydrate (16.5 mmol) and water (55.6 mmol) were added to Compound III-4 (11.0 mmol), and the mixture was allowed to react at 80° C. for 11 hours. Water was added to the resultant reaction solution, and the solution was extracted with toluene. An organic layer was washed with a saturated sodium bicarbonate solution and saturated brine, and thereafter dried over anhydrous sodium sulfate and concentrated. The concentrate was purified with the use of a silica gel column. In this way, Compound II-4, which was a desired substance, was obtained.

Yield: 68%

$^1$H-NMR (400 MHz, CDCl$_3$) δ:

1.40-1.57 (1H, m), 1.85-2.10 (3H, m), 2.40-2.52 (2H, m), 2.45 (3H, s), 2.46 (3H, s), 2.92-3.00 (1H, m), 3.65-3.77 (2H, m), 3.80-3.97 (2H, m), 6.97-7.04 (2H, m), 7.17-7.24 (2H, m), 7.30-7.39 (2H, m), 7.60-7.74 (2H, m).

Reference Production Example 3

Synthesis of 2,2-bis(bromomethyl)-5-(4-chlorobenzyl) cyclopentanone (Compound II-5)

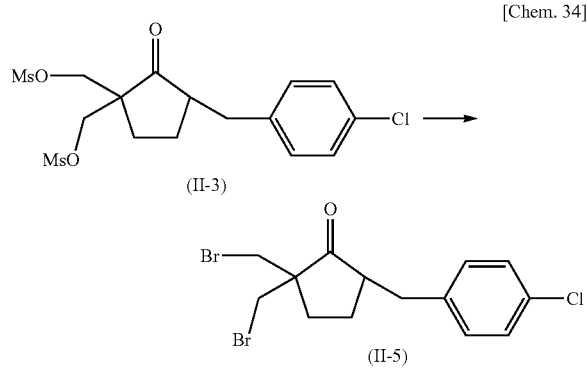

Compound II-3 (4.7 mmol) was dissolved in N-methylpyrrolidone (25 ml). To the solution, lithium bromide (11.5 mmol) was added. The mixture was allowed to react at 90° C. for 9 hours. The resultant mixture was concentrated, and thereafter a 1N hydrochloric acid aqueous solution was added to the mixture. The mixture was extracted with ethyl acetate. After that, the organic layer was washed with water and saturated brine, and dried over anhydrous sodium sulfate. After that, the solvent was distilled off, and the residue was purified with the use of a silica gel column. In this way, Compound II-5, which was a desired substance, was obtained.

Yield: 51%

$^1$H-NMR (400 MHz, CDCl$_3$)δ:
1.50-1.70 (1H, m), 2.02-2.20 (3H, m), 2.50-2.62 (1H, m), 2.65 (1H, dd, J=13.8, 8.5 Hz), 3.08 (1H, dd, J=13.8, 4.3 Hz), 3.27 (1H, d, J=10.8 Hz), 3.30 (1H, d, J=10.8 Hz), 3.49 (1H, d, J=10.3 Hz), 3.53 (1H, d, J=10.3 Hz), 7.05-7.13 (2H, m), 7.22-7.30 (2H, m).

Furthermore, compounds represented by the formula (II), which are listed in Table 1, can be synthesized by the methods in accordance with the above-described Examples and Reference Production Examples. In Table 1 and Table 2 (provided later), each "4-Cl" in the "(X)n" column means that a substituted or unsubstituted benzyl group which is bonded to a cyclopentane ring is a 4-chlorobenzyl group.

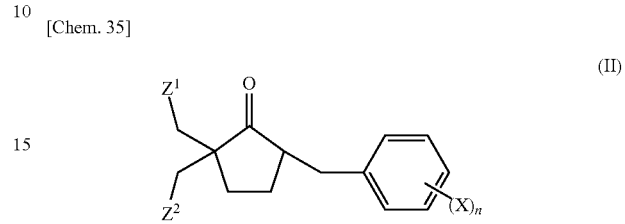

TABLE 1

| Compound Number | Z$^1$ | Z$^2$ | (X)n |
|---|---|---|---|
| II-1 | Cl | H | 4-Cl |
| II-2 | Cl | Cl | 4-Cl |
| II-3 | OMs | OMs | 4-Cl |
| II-4 | OTs | OTs | 4-Cl |
| II-5 | Br | Br | 4-Cl |
| II-6 | I | I | 4-Cl |
| II-7 | Br | H | 4-Cl |
| II-8 | OTs | H | 4-Cl |
| II-9 | OMs | H | 4-Cl |
| II-10 | I | H | 4-Cl |

Note that a compound represented by the formula (II) may have two asymmetric carbon atoms in its structure. In such a case, the compound is a mixture of a pair of diastereomers. Such diastereomers are represented in the following manner: one isomer has "a" at the end of its compound number; and the other isomer has "b" at the end of its compound number. The properties and $^1$H-NMR data of compounds represented by the formula (II) other than those listed in Table 1 are listed in Table 2.

TABLE 2

| Compound Number | Property | $^1$H-NMR (400 MHz, CDCl$_3$)δ |
|---|---|---|
| II-7a | Colorless oil | 0.97 (3H, s), 1.46-1.55 (1H, m), 1.68-1.86 (1H, m), 1.95-2.15 (2H, m), 2.39-2.47 (1H, m), 2.65 (1H, dd, J = 14.0, 8.3 Hz), 3.18 (1H, dd, J = 14.0, 4.5 Hz), 3.32 (1H, d, J = 10.0 Hz), 3.53 (1H, d, J = 10.0 Hz), 7.08 (2H, d, J = 8.5 Hz), 7.23 (2H, d, J = 8.5 Hz). |
| II-7b | Colorless oil | 1.18 (3H, s), 1.60-1.86 (2H, m), 1.95-2.15 (1H, m), 2.19-2.27 (1H, m), 2.55-2.65 (2H, m), 3.00-3.10 (1H, m), 3.22 (1H, d, J = 10.2 Hz), 3.32 (1H, d, J = 10.0 Hz), 7.08 (2H, d, J = 8.5 Hz), 7.23 (2H, d, J = 8.5 Hz). |
| II-9a | Colorless oil | 0.86 (3H, s), 1.49-1.60 (1H, m), 1.69-1.77 (1H, m), 1.97-2.12 (2H, m), 2.40-2.47 (1H, m), 2.69 (1H, dd, J = 14.0, 8.2 Hz), 2.98 (3H, s), 3.05 (1H, dd, J = 14.0, 4.5 Hz), 4.06 (1H, d, J = 9.6 Hz), 4.23 (1H, d, J = 9.6 Hz), 7.10 (2H, d, J = 8.5 Hz), 7.24 (2H, d, J = 8.5 Hz). |
| II-9b | Colorless oil | 1.10 (3H, s), 1.60-1.68 (1H, m), 1.69-1.77 (1H, m), 1.97-2.12 (1H, m), 2.20-2.26 (1H, m), 2.50-2.61 (2H, m), 2.94 (3H, s), 3.03-3.10 (1H, m) 4.00 (1H, d, J = 9.5 Hz), 4.13 (1H, d, J = 9.5 Hz), 7.10 (2H, d, J = 8.5 Hz), 7.24 (2H, d, J = 8.5 Hz). |

Furthermore, similarly, compounds represented by the formula (III), which are listed in Table 3, can be synthesized by the methods in accordance with the above-described Examples and Reference Production Examples.

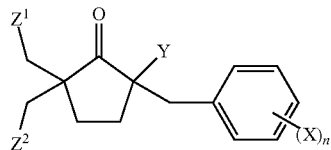
(III)

TABLE 3

| Compound Number | $Z^1$ | $Z^2$ | (X)n | Y |
| --- | --- | --- | --- | --- |
| III-1 | Cl | H | 4-Cl | $CO_2Me$ |
| III-2 | Cl | Cl | 4-Cl | $CO_2Me$ |
| III-3 | OMs | OMs | 4-Cl | $CO_2Me$ |
| III-4 | OTs | OTs | 4-Cl | $CO_2Me$ |
| III-5 | Br | Br | 4-Cl | $CO_2Me$ |
| III-6 | I | I | 4-Cl | $CO_2Me$ |
| III-7 | Br | H | 4-Cl | $CO_2Me$ |
| III-8 | OTs | H | 4-Cl | $CO_2Me$ |
| III-9 | OMs | H | 4-Cl | $CO_2Me$ |
| III-10 | I | H | 4-Cl | $CO_2Me$ |

Note that a compound represented by the formula (III) may have two asymmetric carbon atoms in its structure. In such a case, the compound is a mixture of a pair of diastereomers.

Industrial Applicability

The present invention is suitably applicable to production of an important intermediate for an agricultural fungicide "metconazole".

The invention claimed is:

1. A method for producing a cyclopentanone compound represented by the formula (I)

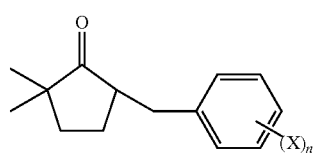
(I)

(wherein X represents a halogen atom, an alkyl group, an alkoxy group, a haloalkyl group, a haloalkoxy group or a phenyl group; n is an integer of 0 to 5; and, when n is 2 or greater, the groups represented by X may be different from each other), the method comprising the steps of:

A) substituting the group represented by Y by a hydrogen atom by allowing a compound represented by the formula (III) or an intermediate compound obtained from the compound represented by the formula (III) to react with a catalyst or a halogenating agent:

(III)

(wherein X and n are as defined for the formula (I); Y represents an alkoxycarbonyl group or a cyano group; $Z^1$ represents a halogen atom or a substituted sulfonyloxy group; and $Z^2$ represents a hydrogen atom, a halogen atom or a substituted sulfonyloxy group); and B) substituting, by hydrogen atoms, (i) the group or the atom represented by $Z^1$ and (ii) the group or the atom represented by $Z^2$ when $Z^2$ is not a hydrogen atom, by reducing the compound represented by the formula (III) or the intermediate compound obtained from the compound represented by the formula (III).

2. The method according to claim 1, wherein:

step A) is obtaining an intermediate compound represented by the formula (II) by allowing the compound represented by the formula (III) to react with an acid catalyst:

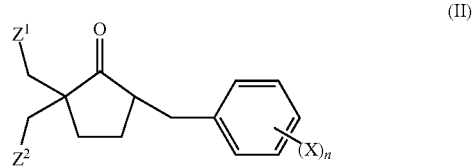
(II)

(wherein X, n, $Z^1$, and $Z^2$ are as defined for the formula (III)); and step B) is obtaining the compound represented by the formula (I) by reducing the intermediate compound represented by the formula (II).

3. The method according to claim 1, wherein:

Y in the formula (III) represents an alkoxycarbonyl group;

step A) is obtaining an intermediate compound represented by the formula (II) by allowing the compound represented by the formula (III) in which Y is an alkoxycarbonyl group to react with a halogenating agent:

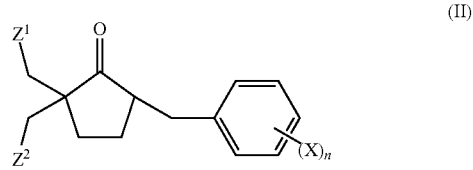
(II)

(wherein X, n, $Z^1$, and $Z^2$ are as defined for the formula (III)); and step B) is obtaining the compound represented by the formula (I) by reducing the intermediate compound represented by the formula (II).

4. The method according to claim 1, wherein:

step B) is obtaining an intermediate compound represented by the formula (IV) by reducing the compound represented by the formula (III):

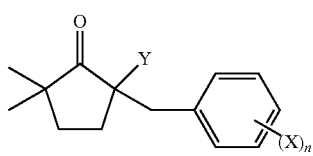

(IV)

(wherein X, n, and Y are as defined for the formula (III)); and step A) is obtaining the compound represented by the formula (I) by allowing the intermediate compound represented by the formula (IV) to react with a catalyst or a halogenating agent.

5. The method according to claim 1, wherein $Z^2$ is a substituted sulfonyloxy group or a halogen atom.

6. The method according to claim 1, wherein $Z^2$ is a hydrogen atom.

7. A method according to claim 5, further comprising the steps of:

obtaining a compound represented by the formula (V) by allowing a compound represented by the formula (VI) to react with formaldehyde or a formaldehyde derivative:

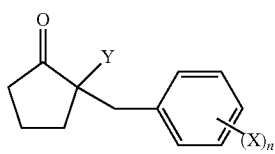

(VI)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; and Y represents an alkoxycarbonyl group or a cyano group):

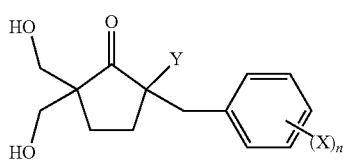

(V)

(wherein X, n, and Y are as defined for the formula (VI)); and obtaining the compound represented by the formula (III) in which $Z^2$ is a substituted sulfonyloxy group or a halogen atom, by allowing the compound represented by the formula (V) to react with a sulfonyl chloride or a halogenating agent.

8. A method according to claim 5, further comprising the steps of:

obtaining a compound represented by the formula (VII) by allowing a compound represented by the formula (VIII) to react with formaldehyde or a formaldehyde derivative:

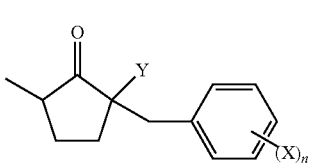

(VIII)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; and Y represents an alkoxycarbonyl group or a cyano group)

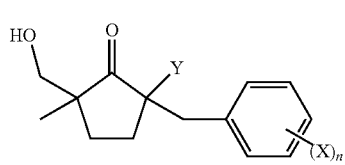

(VII)

(wherein X, n, and Y are as defined for the formula (VIII)); and obtaining the compound represented by the formula (III) in which $Z^2$ is a hydrogen atom, by allowing the compound represented by the formula (VII) to react with a sulfonyl chloride or a halogenating agent.

9. The method according to claim 1, wherein an acid catalyst for use as the catalyst in step A) and a reducing agent for use in the reduction in step B) are added to a reaction system so that both the acid catalyst and the reducing agent are present in the reaction system.

10. The method according to claim 1, wherein the halogenating agent for use in step A) and a reducing agent for use in the reduction in step B) are added to a reaction system so that both the halogenating agent and the reducing agent are present in the reaction system.

11. An intermediate compound represented by the formula (II):

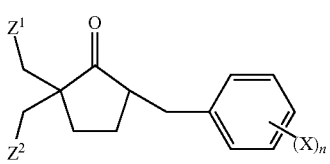

(II)

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; $Z^1$ represents a halogen atom or a substituted sulfonyloxy group; and $Z^2$ represents a hydrogen atom, a halogen atom or a substituted sulfonyloxy group).

12. An intermediate compound represented by the formula (III):

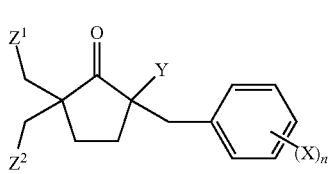

(wherein X represents a halogen atom, an alkyl group, an alkoxy group, a haloalkyl group, a haloalkoxy group or a phenyl group; n is an integer of 0 to 5; when n is 2 or greater, the groups represented by X may be different from each other; Y represents an alkoxycarbonyl group or a cyano group; $Z^1$ represents a halogen atom or a substituted sulfonyloxy group; and $Z^2$ represents a hydrogen atom, a halogen atom or a substituted sulfonyloxy group).

* * * * *